United States Patent
Porschewski et al.

(10) Patent No.: US 8,828,709 B2
(45) Date of Patent: Sep. 9, 2014

(54) QUANTITATIVE DETERMINATION OF PROTEINS FROM FORMALIN-FIXED TISSUE

(75) Inventors: Peter Porschewski, Langenfeld (DE); Karl-Friedrich Becker, Germering (DE)

(73) Assignee: Qiagen GmbH, Hilden (DE)

( * ) Notice: Subject to any disclaimer, the term of this patent is extended or adjusted under 35 U.S.C. 154(b) by 1796 days.

(21) Appl. No.: 11/920,123

(22) PCT Filed: May 10, 2006

(86) PCT No.: PCT/EP2006/062198
§ 371 (c)(1),
(2), (4) Date: Oct. 15, 2008

(87) PCT Pub. No.: WO2006/122898
PCT Pub. Date: Nov. 23, 2006

(65) Prior Publication Data
US 2009/0124510 A1    May 14, 2009

(30) Foreign Application Priority Data

May 19, 2005 (DE) .......................... 10 2005 023 011

(51) Int. Cl.
| | |
|---|---|
| C07K 1/14 | (2006.01) |
| C07K 1/36 | (2006.01) |
| G01N 33/68 | (2006.01) |
| G01N 33/50 | (2006.01) |
| G01N 33/48 | (2006.01) |
| G01N 1/31 | (2006.01) |

(52) U.S. Cl.
CPC ............ G01N 33/6803 (2013.01); C07K 1/145 (2013.01); G01N 1/31 (2013.01); C07K 1/36 (2013.01); G01N 33/5082 (2013.01)
USPC ........................................ 435/272; 435/40.52

(58) Field of Classification Search
USPC ............................................... 435/40.52, 272
See application file for complete search history.

(56) References Cited

U.S. PATENT DOCUMENTS

2006/0223106 A1 * 10/2006 Prockop et al. .................... 435/6

FOREIGN PATENT DOCUMENTS

| WO | WO 2005/116256 A2 | 12/2005 |
| WO | WO 2005/116256 A3 | 12/2005 |

OTHER PUBLICATIONS

Goldenberger et al. 1995. A simple "universal" DNA extraction procedure using SDS and proteinase K is compatible with direct PCR amplification. Genome Research, vol. 4, pp. 368-370.*
Ikeda, K., et al., "Extraction and Analysis of Diagnostically Useful Proteins from Formalin-fixed, Paraffin-embedded Tissue Sections", The Journal of Histochemistry & Cytochemistry, Mar. 1998, pp. 397-403, vol. 46(3), The Histochemical Society, Inc.
Kaplan, B., et al., "Micropurification techniques in the analysis of amyloid proteins", Journal of Clinical Pathology, Feb. 2003, pp. 86-90, vol. 56(2).
Australian Office Action issued in Australian Patent Application No. 2006248997, dated Mar. 25, 2011.

* cited by examiner

*Primary Examiner* — Jon P Weber
*Assistant Examiner* — Kailash C Srivastava
(74) *Attorney, Agent, or Firm* — Fanelli Haag & Kilger PLLC

(57) ABSTRACT

The invention relates to a method with which proteins from formalin-fixed biological samples can be dissolved and subsequently quantified. The method makes it possible to extract intact full-length proteins from the samples and to conduct a subsequent analysis thereof.

20 Claims, 5 Drawing Sheets

Biopsie = biopsy
Formalin-fixiertes Paraffin-eingebettetes Gewebe = Formalin fixed, paraffin embedded tissue
Gewebeschnitte = Tissue sections
Histologie = Histology
Immunhistologie = Immunohistology Unverd. = undiluted
Intaktes protein = intact protein
Korrelation der Signalintensität = Correlation of signal intensity

A

B

C

QUANTITATIVE DETERMINATION OF PROTEINS FROM FORMALIN-FIXED TISSUE

RELATED APPLICATIONS

This application is the U.S. National Phase under 35 U.S.C. §371 of and claims priority to International Application No. PCT/EP2006/062198, filed on May 10, 2006, which in turn claims the benefit of German Application No. DE 10 2005 023 011.3, filed on May 19, 2005, the disclosures of which Applications are incorporated by reference herein.

The present invention relates to a method with which proteins, in particular intact full-length proteins from biological samples fixed in formalin can be solubilised and later quantified.

In many countries fixing tissues in formalin for subsequent histopathological investigation is a standard procedure in order, for example, to differentiate healthy from diseased tissue. Formalin-fixed and paraffin-embedded (FFPE) tissue has been collected for decades and is the source of innumerable diagnostic studies. Tissues from most organs, from different diseases stages, before/during/after therapy, etc. are available. FFPE tissue offers the advantage that the morphology is retained to a high degree. However, owing to crosslinking, macromolecules (DNA, RNA, proteins) can no longer be investigated adequately. According to current opinion, formalin-fixed tissue is unsuitable for isolating proteins routinely and reliably in sufficient amounts for subsequent quantification (e.g. Espina et al. 2003). Accordingly, alternatives to fixing tissues in formalin for subsequent quantification of macromolecules are being sought. Cited here are interalia the freezing of tissue (cryosections) and the currently discussed experimental fixation methods such as, for example, 70% ethanol (e.g. Ahram et al. 2003). Frozen material is indeed an excellent source of macromolecules, but the collection, processing and storage of the tissue is expensive. The experimental fixating methods are a good compromise between maintained morphology and integrity of the macromolecules; however, they play no large role in retrospective studies.

The candidate molecules identified by the human genome project will have to be tested at a protein level for their clinical applicability in large retrospective and prospective investigations. DNA and RNA analyses had previously not been considered feasible with formalin-fixed material. Today such analyses are routine, even following laser-supported tissue microdissection. The same could also apply to protein analysis. The methods for the isolation of nucleic acids differ considerably from those for the isolation of proteins. For example, no proteases may be used in protein isolation, for in this way proteins are digested and are thus no longer intact. The method of Expression Pathology (WO 2004/080579 A2) is concerned precisely with this point and uses proteases in combination with the effect of heat in order to isolate proteolytic fragments—that is, peptides. These can be analysed in subsequent steps by means of mass spectrometry. The method of Expression Pathology thus differs from the method described here. Protein crosslinkages—brought about by formalin—can be broken down by sufficient heat treatment.

The following example of this are known.

(1) Chromatin immunoprecipitation (ChiP). ChiP is a procedure with which it is possible to detect whether a target protein binds in vivo to a certain DNA sequence. Intact cells are fixed with formalin in order to bring about DNA-protein and protein-protein crosslinking. The cells are then lysed and the DNA is cut in order to divide it into smaller fragments. The DNA-protein complexes are then immunoprecipitated by means of an antibody to the target protein. The DNA-protein linkages are then broken down by the action of heat and the proteins are destroyed by proteases. Finally, it is established with the polymerase chain reaction (PCR) whether a certain DNA sequence has been co-immunoprecipitated using the specific antibody. Heat action is here the principle of the break down of the crosslinking caused by formalin.

(2) Antigen retrieval. Antigens frequently lose their immunoreactivity through formalin fixating. Immunohistological studies with many antibodies were therefore only possible within limits. Today methods are available with which the immunoreactivity of most antigens can be recovered (antibody retrieval). The principle here is—after deparaffination and rehydration of the tissue section—the action of heat on the tissue in aqueous solution. However, quantification of the reaction in immunohistochemistry is only possible within limits.

A method for the preparation of a biomolecule lysate is known from WO 2004/080579 A2 in which formalin-fixed tissue samples re-heated in a buffer system and then treated with a proteolytic enzyme in order to degrade the tissue.

There is, however, currently no method available with which intact proteins from formalin-fixed tissue can be reliably investigated quantitatively and sensitively with modern methods. Immunohistochemistry (IHC), the determination of immunoreactivity and assignment to individual cells in the tissue section, is currently the only method with which to investigate proteins on formalin-fixed tissue. However, IHC is only quantifiable within limits. Formalin fixating does indeed maintain the morphology of the tissue excellently, but leads to intensive crosslinking of proteins with one another and with other macromolecules, for example with DNA. Previous attempts to isolate protein from formalin-fixed tissues (e.g. Ahram et al. 2003) failed since they generally provided proteins in very poor yields, are unreliable, are limited only to Western blot investigations (e.g. Ikeda et al. 1998) and frequently do not lead to the detection or quantification of intact proteins. Ikeda et al. describe a method which is indeed suitable for the isolation of proteins from FFPE tissue, but does not lead to a quantitative isolation. The reason for this is that the incubation step at 60° C. is clearly not sufficient to isolate the proteins quantitatively. It must be possible to be able to quantify proteins in the smallest of fixed tissue samples, for example from biopsies. It is not possible with current methods to isolate an adequate amount of protein from such samples, for example for determination with protein arrays. Consequently, these methods are unsuitable to determine disease markers in daily clinical routine. The increasing demand for the quantification of proteins from formalin-fixed tissues cannot be met with Western blots alone, neither in the clinic nor in research. Currently the development of high throughput methods, for example protein arrays, are becoming highly significant. Intact proteins from formalin-fixed tissues are currently considered not investigable with protein arrays (Espina et al. 2003).

The problem of the invention is therefore to provide an improved method for the extraction of proteins from formalin-fixed biological samples.

The problem was solved by a method for the quantitative extraction of proteins from a formalin-fixed biological sample whereby the biological sample is incubated in a buffer at a temperature which is adequate to release the proteins, whereby the buffer contains a detergent and no proteolytically active compound, and the biological sample in the buffer is first boiled and then incubated further at a temperature higher than 60° C. Further improvements of the invention follow from the respective dependent claims.

The invention described here relates to a significant optimisation of protein extraction from fixed biological samples such a tissue samples for subsequent analysis and in particular for the quantification of the proteins which is compatible with current high throughput methods, for example protein arrays, in the clinic and in experimental research. Samples from different disease stages or courses are accessible in this way for analysis and quantification by antibody detection.

Surprisingly the method according to the invention for protein extraction from formalin-fixed tissues provides an excellent result and avoids the disadvantages of the state of the art. The previously used techniques clearly did not lead to success because (a) the sample were heated too briefly (e.g. only 50 seconds at 100° C.; or (b) proteases were used (no intact proteins isolable); or (c) a detergent was indeed used, but no adequate heating of the sample followed (e.g. not higher than 60° C., thus too low a protein yield). Only the use of the method described here, namely for example (a) the use of a protease-free buffer, (b) the use of a detergent AND (c) the higher heating (warmer than 60° C. for longer than 50 seconds) led in an unexpected manner to intact proteins in amounts sufficient for subsequent accurate quantification.

Further detection methods for isolated intact proteins can then be, for example, Western blots, protein array, immuno-precipitation, SELDI-TOF mass spectrometry, ELISA and 2-D gel electrophoresis.

In the following the invention will be further illustrated on the basis of embodiment examples.

Either an intact protein or several intact proteins can be detected and quantified with the present method. Proteins from totally different cell compartments, for example cell nuclei, cytoplasma or the cell membrane, can be isolated reliably and determined quantitatively. The isolated intact proteins may be diluted, that is dilution series and thus internal standard curves can be created. In this way it is possible to ensure that the detection and quantification of the proteins occur in the linear region. When required the proteins can be investigated in advance by Western blot to ensure that no cross reactions of the detection agent used, for example antibodies, take place (only one specific band of the correct size in the Western blot). The quantifiable intact proteins isolated by the method described here supplement in an optimum manner results from immunohistochemical analyses that are already carried out in daily clinic routine. Thus, for the first time the exact and sensitive quantification of intact proteins (a problem of the present invention) and the cellular assignment of protein (immunohistochemistry) are possible in fixed tissue. Known disease markers, for example Her2/neu in mammary cancer patients, can now be determined clinically with an accuracy previously unknown. Moreover, new disease markers can be identified comparatively between a healthy and a diseased tissue by the method in which the isolated intact proteins are analysed by conventional protein methods, for example mass spectrometry. Animal tissues can also be investigated with the present method. Animal models are already available for many human diseases, for example tumour diseases. The animal tissues are typically fixed in formalin, embedded in paraffin and examined histopathologically. The present method for protein isolation can be used for a precise, sensitive and efficient quantification of known and new disease markers in this model, for example by protein arrays. It is a further problem of this invention to provide an application pack (a "kit") with which intact proteins from formalin-fixed human or animal biological samples such as tissue can be isolated reliably and in high yield. Components of this application pack are, for example, at least (a) a protease-free buffer system and (b) a detergent. A detailed protocol for protein isolation from formalin-fixed tissues can be included with the application pack.

The present method can be used for both clinical research and fundamentally orientated investigations. Still more important is that the method described here for the isolation of proteins from formalin-fixed tissue can be optimally incorporated into daily clinical routine. In this way significantly more precise diagnostic and therapeutic methods can be employed.

Figure 1:
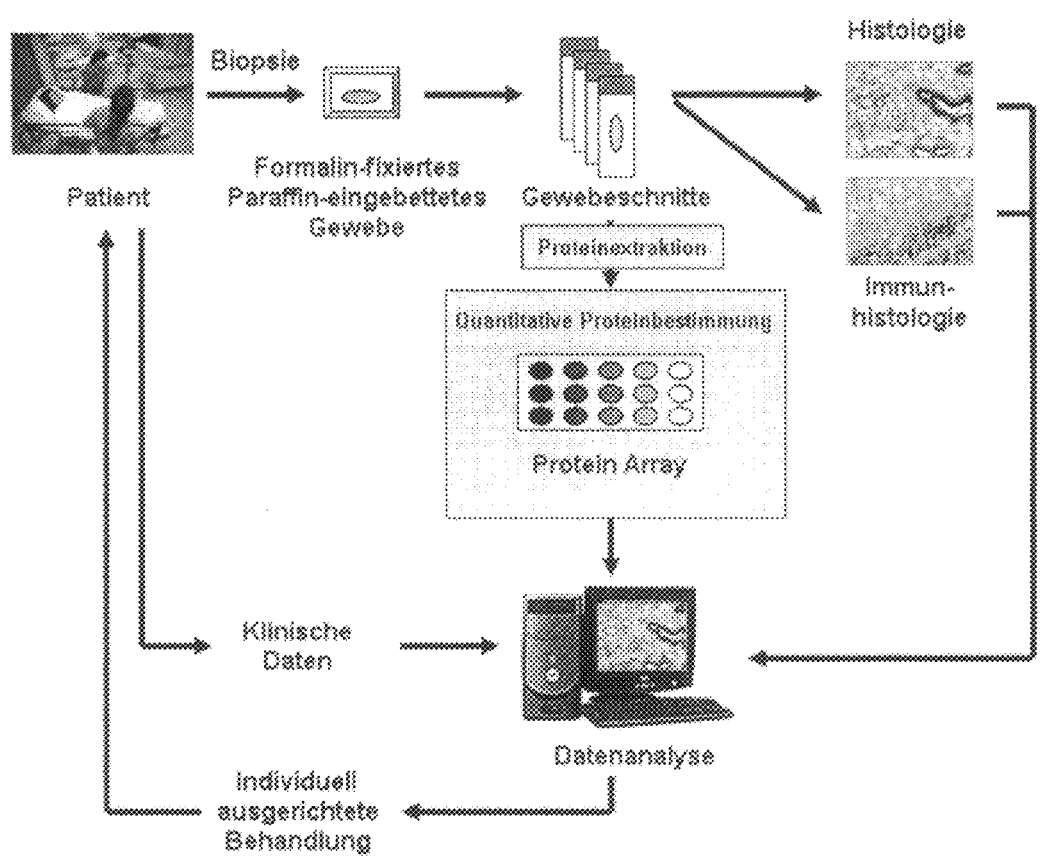
FIG. 1 shows an example of a clinical application of the method according to the invention.

FIG. 1 shows an example of the clinical application of intact proteins from routinely formalin-fixed tissues. In this way even chemically modified proteins, for example phosphorylated or glycosylated proteins, can be detected. Thus far only immunohistochemistry is used clinically for protein investigation on formalin-fixed material. The present method of protein quantification provides supplementary information on the expression of known and new disease markers with as yet unknown accuracy in clinical routine.

Through the construction of protein arrays quantitative proteome investigation is on its way to becoming a part of clinical routine. However, formalin-fixed tissue samples cannot be investigated currently with these high throughput methods owing to poor protein yields. The present method removes this deficiency. Three exemplary strategies of microarrays for detecting proteins which can be incorporated into the present method will be described here. 1. The so-called sandwich immunoarray (antibody array I). In this form of array a protein-binding molecule, for example an antibody, is coupled to a solid surface. The proteins isolated according to the method described (antigens) are specifically bound by the antibody and can then be detected with a second specific antigen-binding antibody, which is tagged for detection. 2. Antigen capture array (antibody array II). Here too, protein binding molecules, for example antibodies, are coupled to a solid surface. The proteins isolated according to the present method are coupled with a detection agent, for example a fluorescent dye and then first bound specifically by the antibody. In this way bound proteins can be detected directly. By comparison of isolated proteins from different tissues, e.g. from tumour tissue and normal tissue the relative amount of the protein of interest can be displayed comparatively by the use of different fluorescent dyes (e.g. Cy-3 and Cy-5). 3. Direct protein array (reverse phase protein array). In this method the proteins isolated according to the method described are dropped directly onto a suitable surface, for example nitrocellulose or polyvinydene difluoride (PVDF), and the bound proteins detected directly or indirectly with specific antibodies (with a second detection antibody). Signal amplification methods (e.g. CSA from DAKO, Inc., Carpenteria, Calif.) permit a very sensitive and specific detection of proteins in solution. This method is very similar to the known dot blot.

Figure 2:
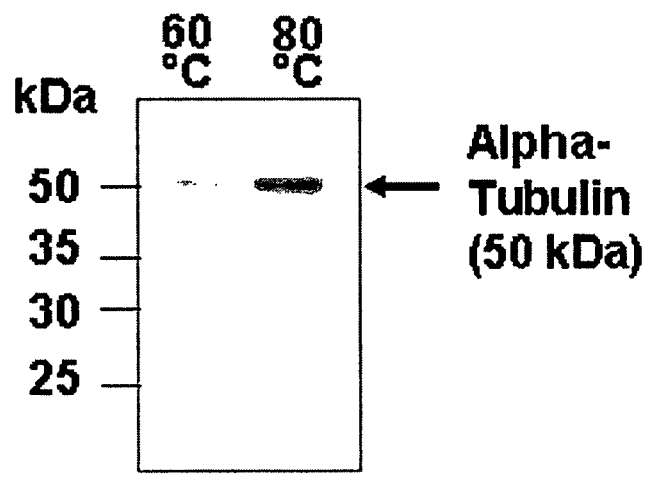
FIG. 2 shows by way of example the improved protein yield by incubation of the tissue samples at warmer than 60° C. Shown is the yield of alpha-tubulin (intact protein, 50 kDa) by Western blot after incubation of the samples at 60° C. (left) in comparison to the method according to the invention (>60° C., e.g. 80° C., right).

The invention provides a method for quantification of proteins from formalin-fixed tissue samples. This technique allows for the first time the precise determination of disease markers in tissue sample under clinic-near conditions. It was discovered in an unforeseeable way that the combination of previously unsuccessful techniques is pivotal for a high yield of intact proteins from fixed tissues required for the investigation of small tissue samples (e.g. biopsies). In previous methods the tissue samples are, for example, first heated to 100° C., followed by a longer period of heating at 60° C. It was discovered that extended heating of the samples at 60° C. is not sufficient to obtain a high yield of protein. Heating the samples to more than 60° C., for example to 80° C., led to a significantly higher amount of dissolved protein (FIG. 2). The method according to the invention can be correspondingly made up of the following steps:

(a) blocks of formalin-fixed and paraffin-embedded tissue samples are cut;

(b) the sections are freed from paraffin;

(c) the tissue areas to be investigated are excised from the tissue section either manually or by laser microscope dissection (optionally the whole tissue can be investigated);

(d) the excised tissue pieces are transferred into a buffer that contains a detergent and is free of proteolytically active compounds. No proteases such as, for example, trypsin or proteinase K may be used in order to ensure the integrity of the proteins;

(e) the samples in the buffer are first boiled (to 95° C. to 100° C.). The incubation time can vary, for example from 5 minutes to 40 minutes. The time of heating can depend, for example, on the size of the sample.;

(f) the samples are then incubated at a temperature above 60° C. (e.g. 80° C.). The incubation time >60° C. can vary, for example from 1 hour to 6 hours. The maximum incubation time at warmer than 60° C. should, however, be less than 16 hours;

(g) intact proteins are now in solution in sufficient amounts and can, for example, be quantified.

In a further preferred embodiment of the method according to the invention an extraction buffer that contains DTT is used. It was established that the use of DTT as reducing agent led to a particularly beneficial yield of isolated intact protein. The advantage of this embodiment lies particularly in that the lysate obtained can be can be quantified directly and particularly well with commercially available protein quantification assays known to the person skilled in the art such as BioRad DC® or BCA assay® from Pierce and used in the further analyses. Dilution of the samples can be dispensed with, thus avoiding measurement inaccuracies, and ensures that the same amounts of protein are used in the subsequent analyses (e.g. Western blot).

FIG. 1 shows an example of a clinical application of the method according to the invention. The high yield of intact proteins from formalin-fixed tissues allows for the first time an integration of histology, immunohistology and quantitative protein expression on routinely obtained biopsy or dissection material. The method allows, for example, the precise investigation of disease markers by protein arrays in different disease stages (premalignant, invasive) or before and after therapy.

FIG. 2 shows as example the improved protein yield by incubation of the tissue sample at warmer than 60° C. The yield of alpha-tubulin (intact protein, 50 kDa) by Western blot after incubation of the samples at 60° C. (left) compared to the method of the invention (>60° C., e.g. 80° C., right) is shown.

Figure 3:
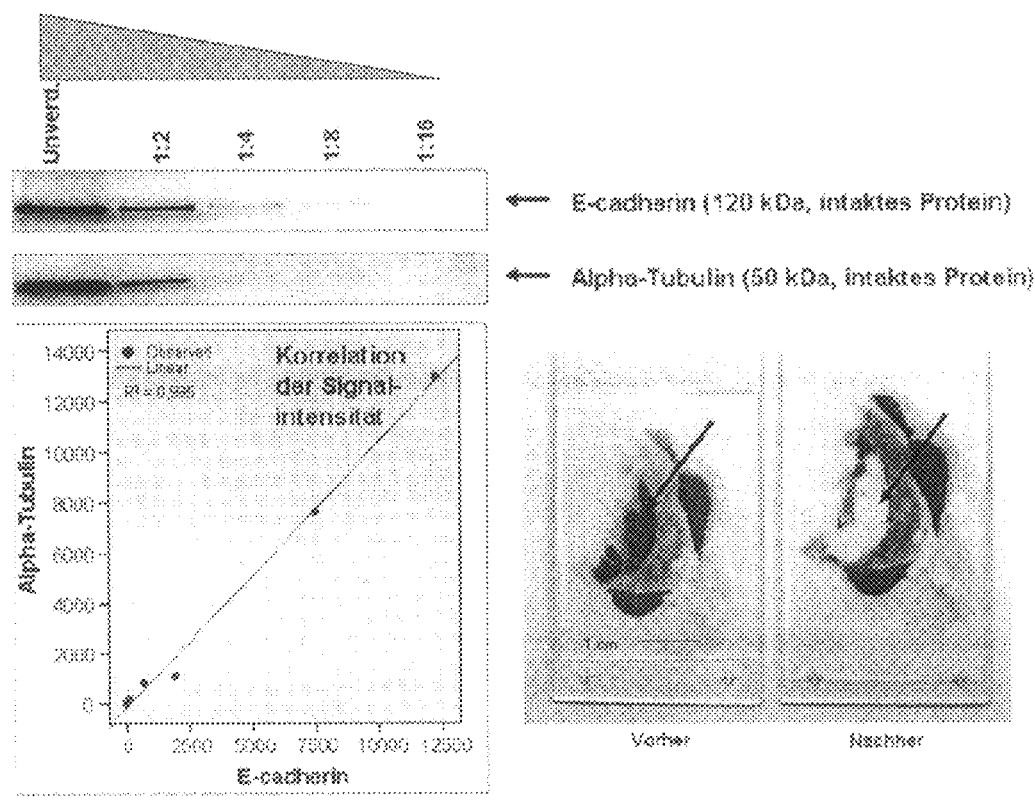
FIG. 3 shows the correlation of two proteins (E-cadherin, alph-tubulin) after extraction from formalin-fixed tissues.

FIG. 3 shows the correlation of two proteins (E-cadherin, alph-tubulin) after extraction from formalin-fixed tissues. The signal intensities of the two proteins correlate excellently with one another, that is intact proteins can be correlated with one another (quantified) after isolation from formalin-fixed tissue. Different dilutions (1:2 to 1:16) of a protein lysate from normal colon tissue are analysed by Western blot. For illustration the tissue is shown before and after scraping from the slide (arrow). Unverd.=undiluted sample.

Figure 4:
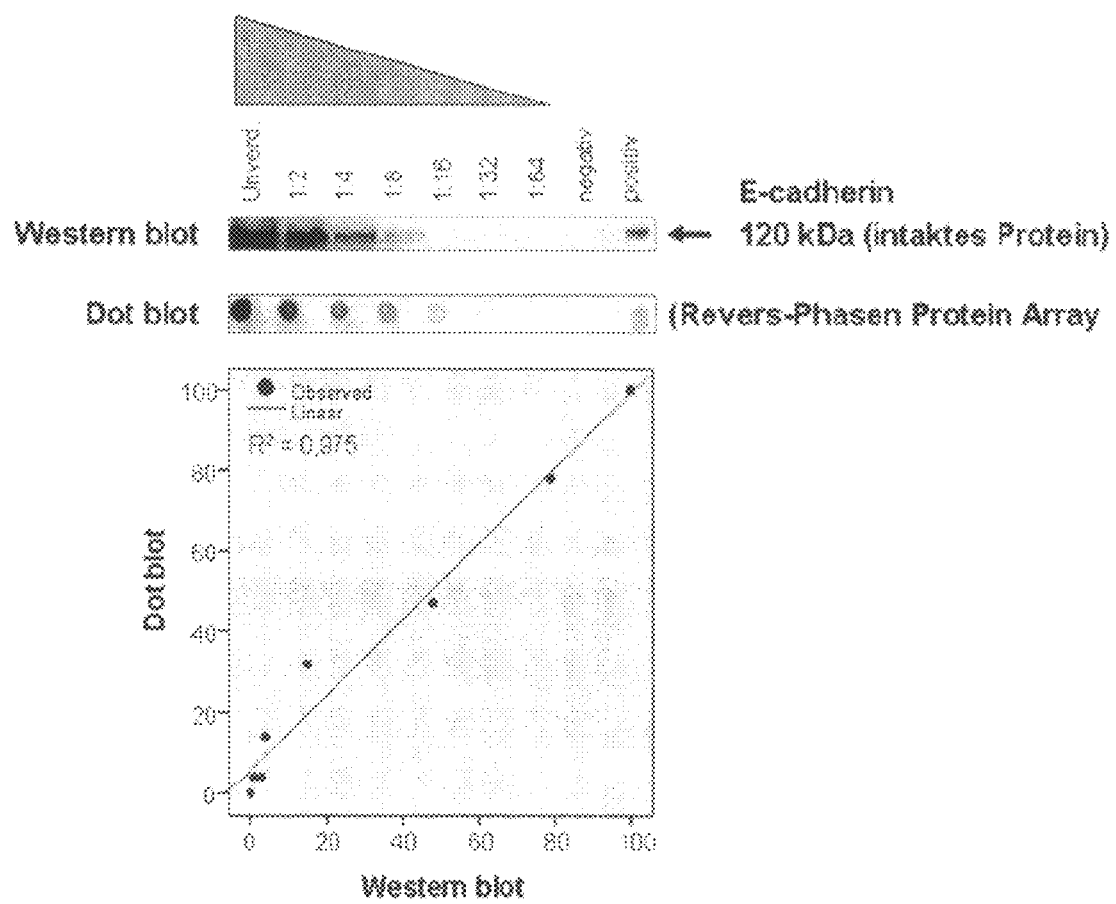
FIG. 4 shows the correlation between Western blot (detection of the intactness of the proteins, demonstration of antibody specificity) and the simplest form of a reverse-phase protein array (dot blot).

FIG. 4 shows the correlation between Western blot (measurement of the integrity of the proteins, demonstration of antibody specificity) and the simplest form of a reverse phase protein array (dot blot). Different dilutions (1:2 to 1:64) of a protein lysate of normal colon tissue are investigated in Western blot and dot blot. In each case percentage values are plotted relative to the undiluted samples for densiometric evaluation (bottom) (undiluted sample=100%). Negative, negative control (extraction buffer); positive control (protein lysate from deep-frozen colon tissue).

Figure 5:
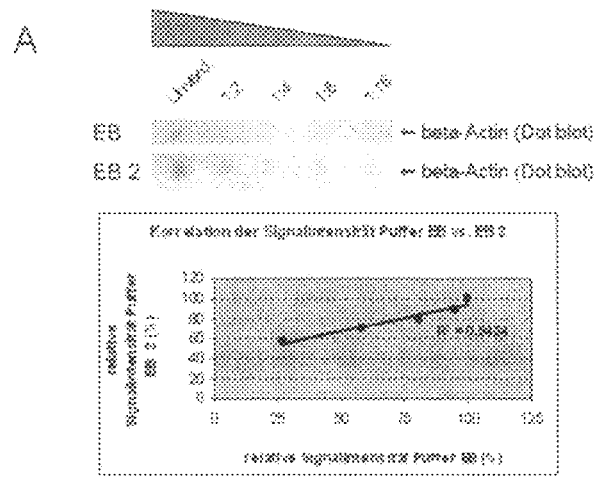
FIG. 5 shows the correlation of beta-actin after extraction from FFPE sections with buffers containing different reduction agents.
Figure 5:
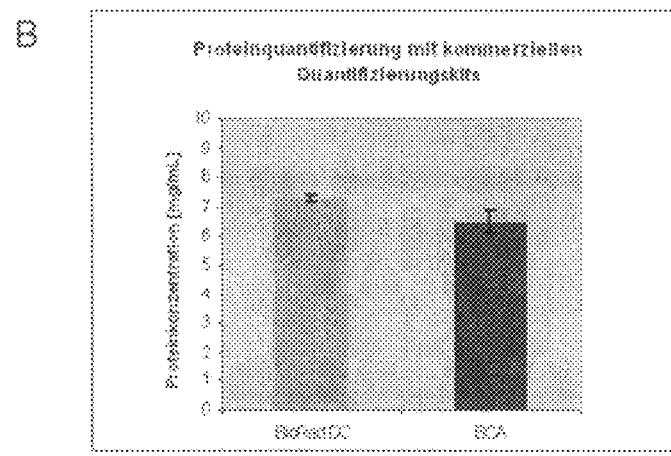
Figure 5:
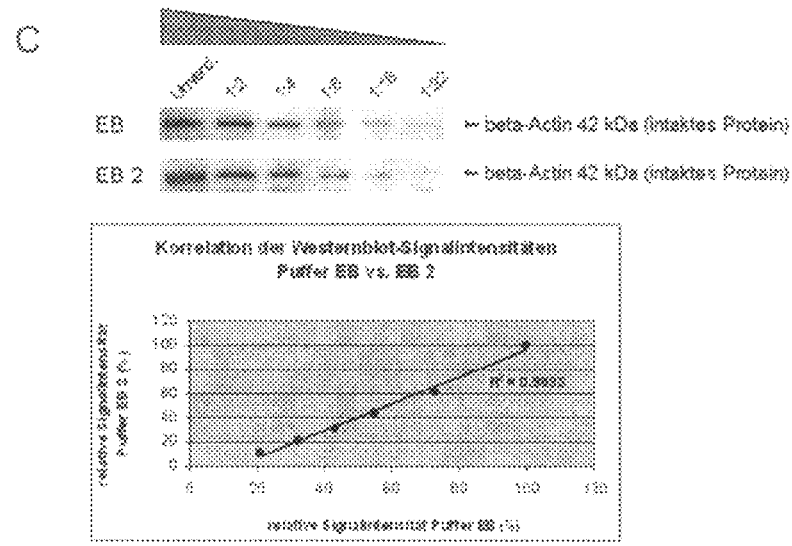

FIG. 5 shows the correlation of beta-actin after extraction from FFPE sections with buffers containing different reduction agents. (A) Intact proteins were isolated from normal brain tissue with the two extraction buffers EB (contains β-mercaptoethanol) and EB 2 (contains DTT). Dilutions of the protein lysates were analysed in the dot blot by β-actin immunocolouration. The signal intensities correlate excellently. (B) The protein concentration of the protein lysate prepared with the extraction buffer EB 2 was determined with commercially available protein quantification kits. (C) On the basis of the protein quantification with the protein quantification kits and the correlation in the dot plot each of 20 μg of the two protein lysates were separated in SDS-PAGE and the amount of β-actin determined in the Western blot. The signal intensities from the two samples correlate well and can be quantified.

Buffers or buffer systems within the meaning of the invention relate to a buffer with a specific pH value within the range of 1.0 to 9.0.

All detergents known to the person skilled in the art and suitable for cell lysis can be used as detergents for the method according to the invention. In particular SDS, sodium deoxycholate, CHAPS, Triton X100, Nonidet P40 or Tween 20 are used as detergents.

The concentration of detergent can be, for example, 0.1-10%. Particularly preferred the concentration range lies between about 1-5%.

Furthermore, the buffer can comprise additionally reducing reagents such as 1,4-dithio-DL-threit, DTE, TCEP or MEA.

Proteolytically active compounds within the meaning of the invention are understood to comprises all protein-cleaving compounds, for example proteolytic enzymes such as proteases, in particular trypsin, chymotrypsin, papain, pepsin, pronase and endoproteinase Lys-C. Furthermore, proteolytically active compounds within the meaning of the invention are also non-enzymatic substances that are suitable for cleaving proteins, such as bromocyan.

Biological samples within the meaning of the invention can be whole organisms, tissue sections, tissue samples, body fluids, cellular or viral material. Preferably the method according to the invention is used with tissues samples and/or cell cultures. The samples can be human or animal biological samples, but also samples from bacteria, viruses or a monocellular organism.

The biological samples are preferably fixed in formalin and/or fixed in formalin and embedded in paraffin.

The present invention thus describes a method for the extraction of proteins from formalin-fixed biological sample, whereby the biological sample is incubated in a buffer at a temperature that is sufficient to release the proteins, whereby the buffer comprises a detergent and no proteolytically active compound, and the biological sample in the buffer is first boiled and then further incubated at a temperature above 60° C.

The biological sample is preferably boiled in the buffer for 5 to 40 min. Particularly preferred the biological sample is incubated for a period of 20 min to 16 h.

A particular advantage of the present invention is that the released proteins are essentially intact.

The detergent is preferably SDS, sodium deoxycholate, CHAPS, Triton X100, Nonidet P40 or Tween20.

The buffer preferably comprises an additional reducing reagent such as 1,4-dithio-DL-threitol, dithioerythritol (DTE), tris(2-carboxyethyl)phosphine (TCEP) or monoethanolamine (MEA).

When the biological sample is a sample that is fixed in formalin and embedded in paraffin, it is deparaffinated before protein extraction.

An advantage of the method according to invention is than the extracted proteins can be further fractionated.

In particular, the extracted protein can be fractionated in one or several steps.

A further advantage is that the proteins can be subsequently quantified.

The quantification of the proteins is preferably carried out by the method of Lowry or BCA, whereby other quantification methods, in particular protein arrays, can also be used.

The extracted proteins can then be treated further by means of proteolytic enzymes such as trypsin, chymotrypsin, proteinase K, papain, pepsin, pronase, endoproteinase Lys-C, endoproteinase Glu-C—or glycosidases—such as endoglycosidase H, N-glycosidase F, neuroaminidase) or phosphatases.

It is advantageous that the proteins can be used for at least one biochemical assay.

For example, a preferred biochemical assay is a protein array such as a microarray, in particular a sandwich immunoarray, antigen capture array or a direct protein array.

The biochemical assay can preferably serve for the determination of one or several diagnostically or clinically relevant marker proteins.

Thereby the marker proteins from at least two biological samples can be compared with one another. Thus, for example, diseased and healthy can be differentiated. Furthermore, the assay can also be carried out at a higher multiplex level in order to analyse one or more relevant markers Particularly preferred the biological sample is a tissue sample, for example a formalin-fixed sample that is embedded in paraffin.

Particularly preferred the buffer does not contain a protease as proteolytically active compound.

Moreover, the present invention provides a kit for the quantitative extraction of intact proteins from formalin-fixed biological samples comprising
  (a) A buffer system that contains no proteolytically active compound, and
  (b) a detergent.

Preferably the kit comprises SDS, sodium deoxycholat, 3-((3-Cholamidopropyl)dimethylammonio)-1-Propanesulfonic Acid (CHAPS), a non-ionic surfactant having a hydrophilic polyethylene oxide group and a hydrocarbon lipophilic or hydrophobic group (Triton X100), a non-ionic, non-denaturing detergent having an alkenylphenoxypolyethoxide group and an alcohol group (Nonidet P40) or polysorbate-20 (Tween 20) as detergent.

Particularly preferred the buffer does not contain a protease as proteolytically active compound.

EMBODIMENT EXAMPLES

Example 1

Protein Extraction from Formalin-Fixed Tissue

In the following a typical protein extraction according to the present method is described in detail. A significant improvement (high protein yield) of this method in comparison to standard methods is illustrated in FIG. 2. The experience operator will modify somewhat one or other of the steps of the protocol. Buffers with somewhat different compositions and pH values can be used. The use of a detergent, e.g. SDS, the boiling of the sample at 95° C. to 100° C. and the subsequent incubation at more than 60° C. (e.g. 80° C.) are, however, pivotal; in addition no proteases may be used. The times for the respective heat treatment and the volumes of buffer can vary. Also variable is the manual communition of the tissue. It can be carried out mechanically (e.g. with a pestle) or, for example, with ultrasound. Typical times and volumes are listed here. The result of a correlation of two proteins from formalin-fixed tissue is shown in FIG. 3. The first protein array with intact proteins from formalin-fixed tissue is shown in FIG. 4 (reverse phase protein array, dot blot).

Typical Procedure:
1. Prepare 2×10 µm sections from the same paraffin block
2. Deparaffinise sections
2.1. 10 min xylene, repeat 2×
2.2. 10 min 100% ethanol
2.3. 10 min 96% ethanol
2.4. 10 min 70% ethanol
2.5. Transfer sections to distilled water
3. Remove sections from distilled water, dry briefly (but should not dry out)
4. Scrape off tissue area with a canulla
5. Transfer excised tissue on canulla into 100 µl extraction buffer (EB)*(tissue from 2 sections per 1.5 ml reaction vessel)
6. Grind well in extraction buffer with Teflon pestle, place on ice
7. Vortex, place on ice
8. Repeat steps 6 to 7 once
9. Pull solution carefully through syringe carefully several times
10. Vortex, place on ice
11. Vortex, place on ice (if much foam: short centrifugation)
12. 20 min 100 20 C. (water bath)
13. 2 hours 80° C. (shaker, 750 rpm)
14. 15 min centrifugation, 4° C., 12500 rpm
15. Supernatant into fresh 1.5 ml reaction vessel→ready protein lysate Preparation of extraction buffer (EB): T-PER® (Pierce)/Lämmli 1:2
  a. 5× Lämmli buffer stock (without bromophenol blue) 10 ml batch
2.5 ml 1.25 M Tris/HCl (pH 6.8)
4.5 ml glycerol
2.8 ml beta-mercaptoethanol
1 g SDS
to 10 ml with distilled water

[1 M Tris corresponds to 121.14 g; 1.25 M corresponds to 151.43 g 1000 ml-151.43 g; 50 ml-7.6 g; adjust to pH 6.8 with conc. HCl]

b. 2× Lämmli buffer: 1000 µl 5× Lämmli buffer+1500 µdistilled water c. For 5 ml extraction buffer:
2.5 ml T-PER® (Pierce)
+2.5 ml 2× Lämmli buffer
+½ complete Mini Protease Inhibitor tablet (Bayer)
Freeze aliquots at −20° C.

Example 2

Protein Extraction from FFPE Tissue with Alternative Extraction Buffer EB2

In a further embodiment of the method according to the invention DTT (1,4-dithio-DL-threitol) is used. DTT is preferably used in the quantification of isolated proteins, for example with the DC Protein Assay Kit® from the company BioRad or the Micro BCA Assay Kit® from Pierce (FIG. 5)

The SDS concentration and the corresponding incubation times at 100° C. and 80° C. were not changed. The advantage of this embodiment is that the concentration of ready protein lysate can be determined directly with a commercially available protein quantification kit without the components—here the special reducing agent—interfering with the assay. The protein concentration can be better measured in the linear region, if appropriate the sample must then be diluted owing only to the high protein content. In this way a yet more accurate measurement result is obtained and hence the respective amount of protein can be used in down-stream applications.

1. Cut 2×10 µm sections from the same paraffin block and transfer to a reaction vessel
2. Deparaffinise sections
2.1. 10 min xylene, repeat 2×
2.2. 10 min 100% ethanol
2.3. 10 min 96% ethanol
2.4. 10 min 70% ethanol
3. Add 100 µl extraction buffer (EB2)*
4. Vortex, place on ice
5. Pull up solution carefully into a pipette several times
6. Vortex, place on ice (if much foam: short centrifugation)
7. 20 min 100° C. (water bath)
8. 2 hours 80° C. (shaker, 750 rpm)
9. 15 min centrifugation, 4° C., 12500 rpm
10. Transfer supernatant into a fresh 1.5 ml reaction vessel→ready protein lysate
11. Quantification by commercial protein quantification kit
   Alternative extraction buffer 2 (EB2)
   90 mM Tris/HCl (pH 6.8)
   20% glycerol
   2% SDS
   1 mM DTT (1,4-dithio-DL-threitol)
   Freeze aliquots at −20° C.

The invention claimed is:

1. A method for the extraction of proteins from a formalin-fixed biological sample, comprising incubating the formalin-fixed biological sample in a buffer at a temperature that is sufficient to release the proteins, wherein the buffer comprises a detergent and no proteolytically active compound, and the biological sample in the buffer is first boiled and then incubated further at a temperature greater than 80° C. but is not further boiled.

2. The method according to claim 1, wherein the biological sample is boiled in the buffer for 5 to 40 minutes.

3. The method according to claim 1, wherein the biological sample is incubated at a temperature above 80° C. for a period of 20 minutes to 16 hours.

4. The method according to claim 1, wherein the released proteins are intact.

5. The method according to claim 1, wherein the detergent is sodium dodecyl sulphate (SDS), sodium deoxycholate, 3-((3-Cholamidopropyl)dimethylaminonio)-1-Propanesulfonic Acid (CHAPS), a non-ionic surfactant having a hydrophilic polyethylene oxide group and a hydrocarbon lipophilic or hydrophobic group (Triton X100), a non-ionic, non-denaturing detergent having an alkenylphenoxypolyethoxide group and an alcohol group (Nonidet P40) or polysorbate-20 (Tween20).

6. The method according to claim 1, wherein the buffer additionally comprises at least one reducing agent selected from the group consisting of 1,4-dithio-DL-threitol, dithioerythritol (DTE), tris (2-carboxyethyl)phosphine (TCEP) or monoethanolamine (MEA).

7. The method according to claim 1, wherein the biological sample, when it is a formalin-fixed sample embedded in paraffin, is deparaffinated before the protein extraction.

8. The method according to claim 1, wherein after extraction the proteins are further fractionated.

9. The method according to claim 1, wherein the extracted proteins are subsequently quantified.

10. The method according to claim 1, wherein the extracted proteins are treated with at least one proteolytic enzyme selected from the group consisting of trypsin, chymotrypsin, proteinase K, papain, pepsin, pronase, endoproteinase Lys-C, and endoproteinase glu-C or at least one glycosidase selected from the group consisting of endoglycosidase H, N-glycosidase F, neuroaminidase and phosphatases.

11. The method according to claim 1, wherein the proteins are used for at least one biochemical assay.

12. The method according to claim 1, wherein the biological sample is a tissue sample.

13. The method according to claim 1, wherein the proteolytically active compound is a protease.

14. The method according to claim 1, wherein the sample is incubated at a temperature above 80° C. for more than 50 seconds.

15. The method according to 8, wherein the extracted proteins are fractionated with one or several method stages.

16. The method according to claim 9, wherein the quantification of the proteins is carried out by the method of Lowry or the bicinchoninic acid (BCA) method.

17. The method according to claim 11, wherein the biochemical assay is a protein array.

18. The method according to claim 11, wherein the biochemical assay is used to identify one or more diagnostically or clinically relevant marker proteins present in the biological sample.

19. The method according to claim 17, wherein the protein array is a sandwich immunoarray, an antigen capture array or a direct protein array.

20. The method according to claim 18, wherein the marker proteins from at least two biological samples are compared with one another.

* * * * *